(12) United States Patent
Campbell

(10) Patent No.: US 9,668,927 B2
(45) Date of Patent: Jun. 6, 2017

(54) PRESSURE RELIEF COMPLIANCE SYSTEM AND METHOD FOR MONITORING TIME SPENT APPLYING OR RELEASING PRESSURE

(71) Applicant: Jonathan Campbell, Herndon, VA (US)

(72) Inventor: Jonathan Campbell, Herndon, VA (US)

(73) Assignee: Jonathan Phillip Campbell, Herndon, VA (US)

( * ) Notice: Subject to any disclaimer, the term of this patent is extended or adjusted under 35 U.S.C. 154(b) by 0 days.

(21) Appl. No.: 14/829,254

(22) Filed: Aug. 18, 2015

(65) Prior Publication Data

US 2016/0049062 A1    Feb. 18, 2016

Related U.S. Application Data

(60) Provisional application No. 62/038,315, filed on Aug. 17, 2014.

(51) Int. Cl.
  *G08B 23/00*    (2006.01)
  *A61G 5/10*    (2006.01)
  *A61B 5/00*    (2006.01)

(52) U.S. Cl.
  CPC ............. *A61G 5/10* (2013.01); *A61B 5/447* (2013.01); *A61B 5/6894* (2013.01); *A61G 2203/34* (2013.01)

(58) Field of Classification Search
  CPC ...... A61G 5/10; A61G 2203/34; A61B 5/447; A61B 5/6894
  USPC ....... 340/573.1, 573.4, 10.1, 539.12, 426.32; 600/300, 587
  See application file for complete search history.

(56) References Cited

U.S. PATENT DOCUMENTS

| | | | |
|---|---|---|---|
| 4,554,930 A | 11/1985 | Kress | |
| 6,030,351 A * | 2/2000 | Schmidt | A61B 5/1036 600/592 |
| 7,378,975 B1 * | 5/2008 | Smith | A61B 5/1126 340/573.1 |
| 8,558,702 B2 * | 10/2013 | Smith | A61B 5/00 340/573.1 |

\* cited by examiner

*Primary Examiner* — Dhaval Patel
(74) *Attorney, Agent, or Firm* — Duane Morris LLP

(57) ABSTRACT

In some embodiments, a pressure-sensitive mat and a monitoring device are part of a pressure relief compliance system. The pressure-sensitive mat is placed between a seat cushion and a chair. When a user sits on the cushion, the system will monitor the time the person spends applying pressure and will notify a user with an alarm or by other means when the preset sitting limit is reached. Also a novel method for measuring and adjusting the amount time spent applying and releasing pressure. In some embodiments, rather than simply measure time spent applying pressure, the system will allow the user to "buy back" sit time when the user releases pressure. The rate at which the system will credit the user with a "buy back" of sitting time may in some embodiments be directly proportional to the amount of time the user spends performing a pressure release.

28 Claims, 13 Drawing Sheets

PRESSURE RELIEF COMPLIANCE SYSTEM AND METHOD FOR MONITORING TIME SPENT APPLYING OR RELEASING PRESSURE

CROSS-REFERENCE TO RELATED APPLICATION

This application claims priority to U.S. Provisional Application No. 62/038,315 filed on Aug. 17, 2014, the entirety of which is hereby incorporated by reference herein.

FIELD

The present disclosure generally relates to systems and methods for pressure relief compliance that are useful for preventing or minimizing the occurrence of pressure ulcers. More specifically, some embodiments of the present disclosure are directed to systems and methods for measuring and monitoring pressure applied to a portion of the body of a person and for providing warnings regarding skin-pressure conditions to a user.

BACKGROUND

Able-bodied individuals with normal pressure sensation avoid acquiring pressure sores by subconsciously moving and shifting their weight so that no single area is over-exposed to constant pressure. However, pressure ulcers are a common complication among elderly, diabetic and spinal cord injured ("SCI") populations. Impaired sensation in affected areas can lead to a patient failing to recognize warning signs such as pain and discomfort on areas of the skin that have pressure applied. These areas often include, but are not limited to, bony prominences such as the heel, the coccyx, and ischial tuberosities (the "sit bones"). While pressure sores are usually preventable, these injuries can disrupt rehabilitation or interfere with work, school or community reintegration. Severe pressure sores can lead to a decrease in a person's mobility and independence and can lead to further disability, fatal infections and may ultimately require surgical intervention. Depending on the severity of the injury, a patient's treatment of pressure ulcers can take weeks or even months. Nationwide treatment has been estimated to cost more than $1.2 billion annually.

The prevention of pressure ulcers begins immediately after injury and is a lifelong commitment for those with SCI (or other conditions) and their caregivers. Prevention requires education and vigilance and may involve: regular examinations of skin on areas that receive pressure; limiting moisture and keeping skin as dry as possible; building an individually-prescribed, custom wheelchair cushion and seating system; making necessary changes to diet such as limiting alcohol intake and eating a balanced diet; and, monitoring a person's weight changes.

Current standards of care for SCI individuals suggest a pressure relief procedure be performed by leaning forward, leaning from side-to-side, or lifting up every 15 to 30 minutes for 30 to 120 seconds in order to minimize or prevent the development of pressure ulcers. The particular techniques for performing a pressure relief procedure (sometimes referred to as a pressure release or simply a release) are dependent on the abilities of the individual. For example, individuals who are unable to relieve pressure manually can release pressure by reclining in a powered chair.

SUMMARY

Some embodiments are directed to systems or methods for measuring time spent applying pressure on the skin by sitting and reinforcing the habit of regular pressure releases by the user. Specifically, the disclosure relates to novel systems and methods for measuring and indicating the amount of time spent applying and releasing pressure as well as adjusting sit timers, sit-time limits and alarm limits.

In some embodiments, a system includes at least one sensor capable of measuring force or pressure applied by a portion of the body of a user; a speaker; a memory; and a processor. The processor is operably coupled to receive force or pressure measurements from sensor(s) and is programmed to: initialize a sit timer in the memory; run the sit timer while the force or pressure measured by the at least one sensor is greater than a release threshold; cause the speaker to sound an alarm in an event the sit timer reaches a predetermined sit time limit before the user performs a release having a predetermined full release duration; detect a first release event occurring prior to the sit timer reaching the sit time limit, wherein the measured force or pressure is less than the release threshold during the first release event; and based on the detected first release event, provide the user additional time until the alarm is sounded.

In some embodiments, a system includes at least one sensor capable of measuring force or pressure applied by a portion of the body of a user; a speaker; a memory; and a processor. The processor is operably coupled to receive force or pressure measurements from sensor(s) and is programmed to: initialize a sit timer in the memory; run the sit timer while the force or pressure measured by the at least one sensor is greater than a release threshold; cause the speaker to sound an alarm in an event the sit timer reaches a predetermined sit time limit before the user performs a release having a predetermined full release duration; detect a release event occurring after the sit timer reaches the sit time limit, wherein the measured force or pressure is less than the release threshold during the release event; cause the speaker to silence the alarm in response to the detected release event; and in response to the detected release event, provide the user additional time until the alarm is next sounded.

In some embodiments, a method includes measuring, with at least one sensor, force or pressure applied by a portion of the body of a user. A sit timer is initialized in a memory. The method includes running the sit timer while the force or pressure measured by the at least one sensor is greater than a release threshold. An alarm is sounded in an event the sit timer reaches a predetermined sit time limit before the user performs a release having a predetermined full release duration. The method includes detecting a first release event occurring prior to the sit timer reaching the sit time limit, wherein the measured force or pressure is less than the release threshold during the first release event. Based on the detected first release event, the user is provided additional time until the alarm is sounded.

In some embodiments, a method includes measuring, with at least one sensor, force or pressure applied by a portion of the body of a user. A sit timer is initialized in a memory. The method includes running the sit timer while the force or pressure measured by the at least one sensor is greater than a release threshold. An alarm is sounded in an event the sit timer reaches a predetermined sit time limit before the user performs a release having a predetermined full release duration. The method includes detecting a release event occurring after the sit timer reaches the sit time limit, wherein the measured force or pressure is less than the release threshold during the release event. The alarm is silenced in response to the detected release event. In response to the detected release event, the user is provided additional time until the alarm is next sounded.

In some embodiments, a system includes a sensor, an alarm device, a memory device, and a processor. The sensor is capable of measuring a force or pressure applied by a portion of a user's body. The memory device is capable of storing a first time duration value. The processor is operably connected to the sensor, the memory, and the alarm device. The processor receives from the sensor a sensor signal representative of the measured force or pressure. The processor is programmed to: initialize a sit timer; run the sit timer while the sensor signal is greater than a first threshold; determine, for the condition where the sit timer has run for a time less than the first time duration value, a release event, wherein the release event has a release event duration which begins when the sensor signal is less than a second threshold and ends when the sensor signal is greater than the first threshold; calculate a time duration offset as a function of the release event duration; calculate a second time duration value from the first time duration value and the time duration offset; and send an alarm signal to said alarm device for the condition where: no release event was determined and the sit timer runs for a time not less than the first time duration value, or a release event was determined and the sit timer runs for a time not less than the second time duration, wherein said alarm device activates an alarm upon receipt of the alarm signal.

BRIEF DESCRIPTION OF THE DRAWINGS

The appended figures illustrate the methods and systems of the present disclosure although it will be understood that such figures are in accordance with some embodiments of the disclosure and, therefore, are not to be considered as limiting the scope of the disclosure with regard to other embodiments which the present disclosure contemplates. The following will be apparent from elements of the figures, which are provided for illustrative purposes and are not necessarily to scale.

DETAILED DESCRIPTION

Figure 1:
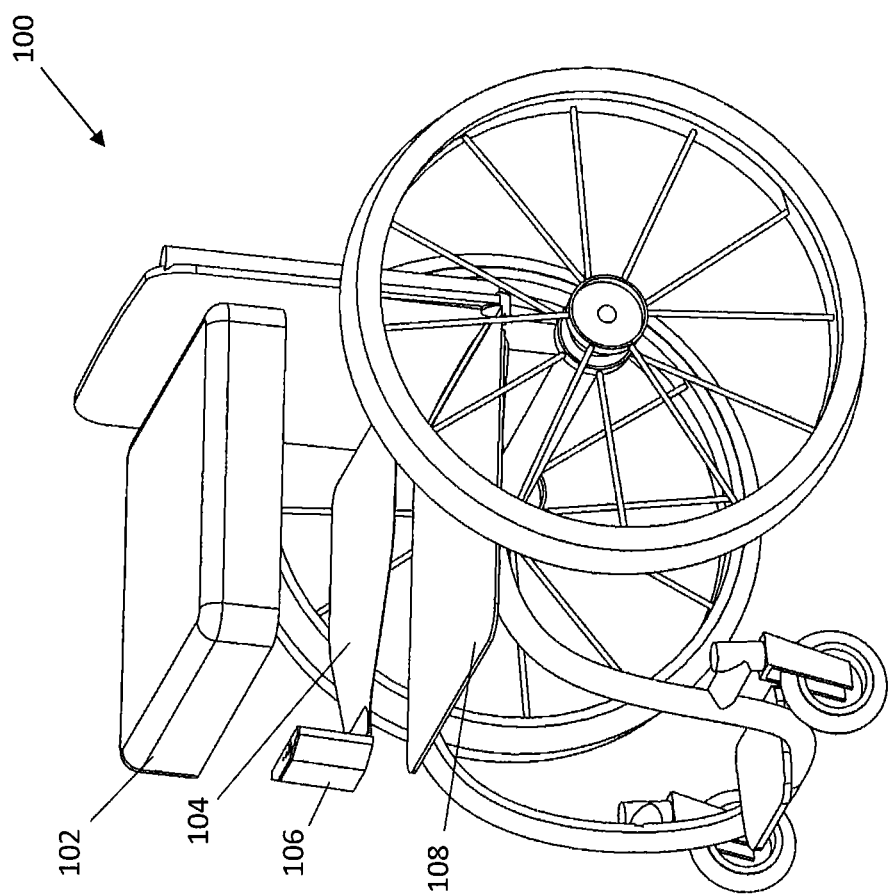
FIG. 1 is an exploded, perspective view of a pressure monitoring system in accordance with some embodiments of the present disclosure.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "vertically," "downwardly," "upwardly," etc.) should be construed to refer to the orientation as then described or as shown in the drawing under discussion. These relative terms are for convenience of description and do not require that the apparatus be constructed or operated in a particular orientation.

Various embodiments provide techniques for monitoring the time spent applying pressure to a user's skin while incentivizing the user to perform pressure releases and while flexibly accommodating a user's needs. For example, the user is incentivized to perform pressure releases because failure to perform an adequate pressure release (e.g., a pressure release lasting at least a predetermined duration) within a predetermined time may result in an alarm sounding. The user may be incentivized to perform such pressure releases frequently through a "buy-back" technique that rewards the user (e.g., in the form of additional time provided before an alarm sounds) each time the user performs a pressure release. In some embodiments, If the user does not perform an adequate pressure release in a timely manner, thereby causing the alarm to sound, functionality is provided to enable the user to temporarily silence the alarm by performing a partial pressure release. This functionality relating to a temporary silencing of the alarm may referred to as snooze functionality.

Figure 2:
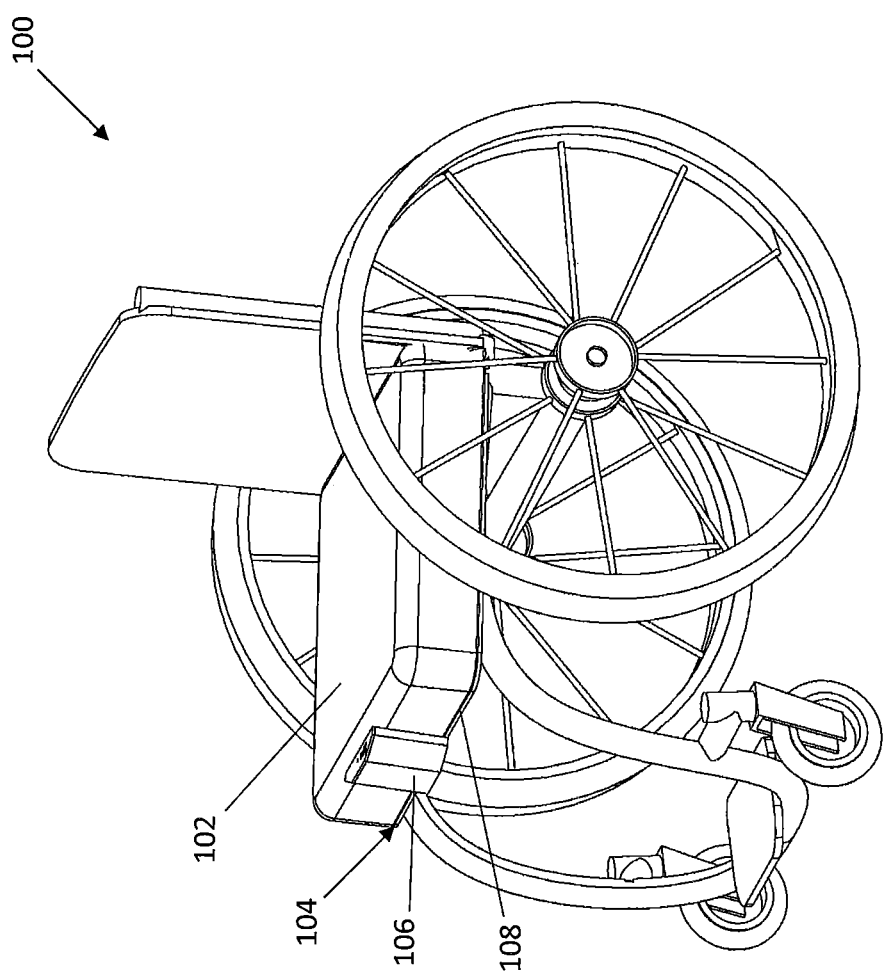
FIG. 2 is a collapsed view of the system of FIG. 1 in accordance with some embodiments of the present disclosure.

An illustrative embodiment of a wheelchair-based pressure monitoring system 100 is shown in FIGS. 1 and 2. The example shown in FIGS. 1 and 2 involves a wheelchair, but other examples may use other types of equipment and do not require a wheelchair. System 100 includes a wheelchair seat cushion 102, a sensor mat 104, a microprocessor unit 106, and a wheelchair seat base 108. FIG. 1 illustrates an exploded, perspective view of these elements, and FIG. 2 shows these elements in their normal positions. The microprocessor unit 106 is operably coupled to the sensor mat 104, which is placed between the wheelchair seat cushion 102 and wheelchair seat base 108.

In some embodiments, sensor mat 104 comprises a pressure sensitive mat embedded with one or more piezoresistive force sensors. When a user sits down on the chair of system 100, the user's weight is detected and measured as a force by the sensor(s) which generate(s) a signal, proportional to the force, which is sent to the microprocessor unit 106. The system is calibrated to convert the signals from these sensors into a pressure placed on the skin of the system user. As person of ordinary skill in the art ("POSA") will understand, pressure and force may be used interchangeably throughout this disclosure in the context of sensors, as pressure is force per unit area and a POSA knows how to perform the relevant conversions. The force sensor(s) of sensor mat 104 may be operably connected to generate a single, combined output signal from the mat 104 to the microprocessor unit 106. In some embodiments, the sensor mat 104 comprises a plurality of sensors, with each sensors measuring a defined area of the sensor mat 104, which outputs a discrete signal for each sensor. This allows the system to measure not only an average pressure or force on a user's skin but the particular pressure or force on any pressure point or particular location. The defined areas may also comprise the left and right, front and back, or other regions of the chair.

While the sensor mat 104 is shown in FIGS. 1 and 2 as a separate component, the sensor mat 104 may be integrated with the wheelchair seat cushion and/or base 102, 108. Furthermore, the sensor mat 104 may be used in other applications in which a person's skin may be at risk overexposure to pressure forces. For instance, in some embodiments the mat 104 is integrated on the arm or foot rests or back support or other additional areas of wheelchair, on the contact point of a crutch, in a bed, or in the clothing of a person at risk of pressure problem areas. For example, sensors or a sensor mat 104 could be placed in the heels of a patient's shoes. These additional sensors may be connected via wires or wirelessly to a microprocessor unit. In these embodiments, the system may monitor every connected sensor and provide notifications to the patient.

While shown in FIGS. 1 and 2 as a unitary device positioned adjacent to the sensor mat 104, the microprocessor unit 106 may comprise a plurality of separate components located elsewhere in the system. The microprocessor unit 106 may comprise a microprocessor, dip switches, mobile device or other programming or user interface, internal memory, indicator LEDs or other display device, speaker, vibrating or other physical indicator and a power source. The power source may be, for example, a rechargeable lithium ion battery dedicated to powering the system 100, or it may be the power source of a powered wheelchair, or power from another source such as an electrical outlet on a wall.

Figure 3:
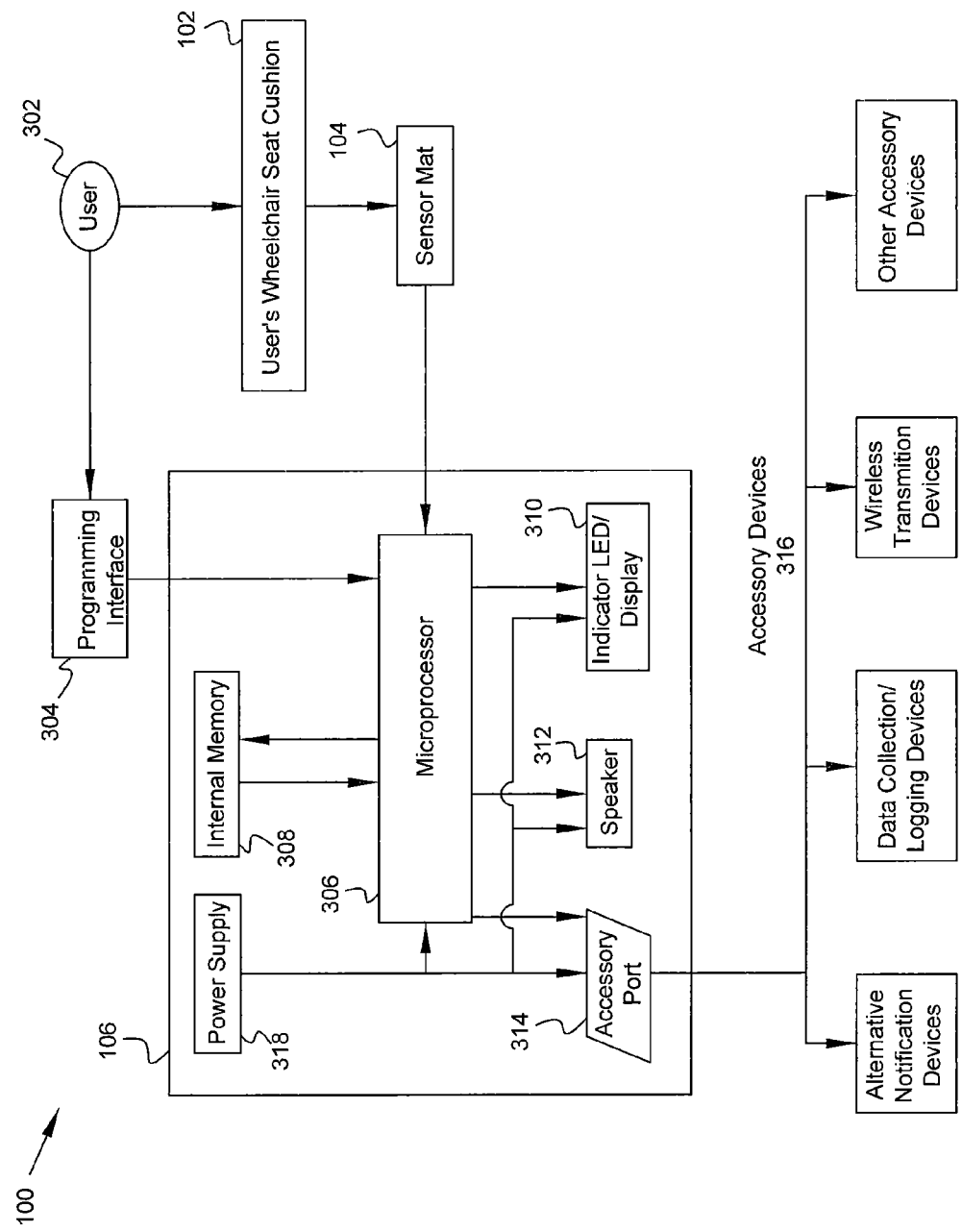
FIG. 3 is a system diagram of operable connections of the components of a pressure monitoring system in accordance with some embodiments of the present disclosure.

A system diagram of the operable connections between the components of a pressure monitoring system, including a detailed diagram of components of a microprocessor unit 106, is shown in FIG. 3. A user 302 may enter system set points/limits and other parameters using a programming or user interface 304, such as a keypad, handheld device or a computer. The user's presets are stored on internal memory or flash drive 308 by the microprocessor 306. The user sits on wheelchair seat cushion 102, thereby applying sitting pressure. In turn, the user's seat cushion 102 applies pressure to sensor mat 104 which may be embedded with piezoelectric force sensors or other force or pressure sensors. The microprocessor 306 receives the user's presets from the programming interface 304 and stores it in internal memory 308 in addition to receiving pressure signals from the sensor mat 104. The microprocessor 306 calculates sit-time and compares it to the user's presets stored in internal memory 308. The sit-time is the time during which the detected pressure is above a calculated threshold limit. If the sit-time has reached the preset sit-time limit, a signal is sent to the speaker 312 and indicator LED or display 310 to generate an alarm or other indication. In some embodiments, the microprocessor 306 may also provide signals to the speaker 312 and/or indicator LED 310 to provide any of the following: status updates; present pressure of the combined or individual sensor(s) in sensor mat 104; present sit time (i.e., accumulated sit time); sit pressure as a percentage of the average, a maximum, or of a threshold value; absolute sit pressure; elapsed time since the last pressure release event; and power supply battery level. A release event is when the user moves such that the detected pressure falls below a predetermined threshold value. The system 100 may include an accessory port 314 which receives power from the power supply 318 and data from the microprocessor 306, such as user presets, sit-time, alarm status, and battery level. Accessory devices 316 connect to the accessory port 314 and receive data from the microprocessor 306. The accessory port 314 may provide a USB, coaxial, fiber optic cable or other connector.

The LED or display 310, or other accessory device 316 may be used to provide user feedback with audible, visual or some other physical feedback mechanism. The system can be programmed to provide this feedback to communicate various types of information, for example: present pressure; passing of some fixed time interval; reaching a goal to perform a specific number of pressure releases without an alarm occurring; time elapsed or remaining on a sit-timer; and, time remaining until alarm will next sound after using the snooze feature, among others. A wireless transmission may be used to transmit stored settings or data records captured by the system for monitoring or sending alerts.

In some embodiments, the microprocessor 306 may be pre-programmed by the user or other person using the programming or user interface 304 to select any combination of settings to include: sit duration or sit time limit (or the "sit time" or "sitting time" limit); minimum release duration or "release duration"; speaker on/off, volume, or tone; vibration notification on/off or patterns; display settings; "snooze" feature on/off; and, "buy back" option on/off. These settings will be stored in the internal memory 308.

The microprocessor 306 may receive signals from the sensor mat 104 when pressure is applied. Upon a user's initial use of the system 300, the microprocessor 306 may calculate the user's average pressure applied by taking several pressure measurements (the output of the sensor mat 104) over a period of time, for example, 10-20 seconds. The average pressure may be an average of one or more combined sensors, or the microprocessor may calculate the average pressure for each sensor individually. The microprocessor may calculate the release threshold. The release threshold may be a percentage of the average pressure of all sensors or of a single sensor, for example, between 70-90% or about 80% of the average pressure. When a signal from the sensor mat 104, whether from individual sensors or a combined sensor output, is interpreted by the microprocessor 306 as corresponding to a pressure less than the release threshold, the microprocessor 306 will register the signal output as a pressure release or release event. Additionally, the microprocessor 306 monitors the amount of time that the signal output from the sensor mat 104 is above or below the release threshold.

In some embodiments, the microprocessor 306 will calculate two or more threshold pressures. These other threshold pressures may comprise different percentages of the calculated average pressure. For instance, the microprocessor may calculate a first pressure threshold to be 80% of the average pressure and a second pressure threshold to be 75% of the average pressure. The microprocessor 306 monitors the signal received from the sensor mat 104. When the signal rises above the first pressure threshold, the microprocessor will run the sit-timer. For convenience, a sit-timer is described in various examples herein, although any type of timer may be used and the user need not be sitting (e.g., a person may be lying in a hospital bed, or standing on crutches, etc.). One of ordinary skill in the art recognizes that the sit-timer (or other type of timer) may be implemented in various ways, e.g., as a variable that is incremented (accumulated), via a function call to an application programming interface (API), etc.

In some embodiments, multiple thresholds are used for pressure release monitoring. For example, when the signal from the force or pressure sensor falls below the second threshold pressure (e.g., 70% of average pressure), the microprocessor will stop the sit-timer and register the pressure decrease as a pressure release and may start a release-timer. The sit-timer will not restart until pressure rises above the first pressure threshold (e.g., 80% of average pressure) again. By using two pressure thresholds in this manner, it is possible to prevent rapid cycling of the sit-timer, alarms, displays and other components that may occur from a user shifting the wheelchair. In some embodiments, the microprocessor 306 may use one or more pressure thresholds and may also require the sensed pressure to be above or below the threshold for a given period of time before registering a shift to or from a pressure release event.

In some embodiments, the microprocessor 306 outputs a signal to drive the indicator LED or display 310. After the average pressure and release threshold are calculated, the microprocessor 306 monitors the amount of time the sensors of mat 104 detect pressure greater than the release threshold and advances a sit timer by an equal amount. As time advances, the indicator LED 310 may change color. For example, the LED 310 may change from greenish to yellowish to reddish hues to indicate the progression of the sit timer as it approaches the sit time limit. In other embodiments, the display may show the time remaining on the sit-timer until an alarm or notification, time since the last pressure release event, or some other display (e.g., a progress bar).

When the device detects that the user has been sitting for the preset sit-time limit, the indicator LED may flash and an audible alarm may play through the speaker or another type of signal may be generated (e.g., a visual cue may be provided to the user, or a signal may be transmitted via wire or wirelessly to a remote station). The alarm will sound until the user takes pressure off the seat (i.e., performs a pressure release). The alarm serves as a negative reinforcement mechanism that essentially punishes the user for not having relieved pressure previously. Although the alarm (e.g., a loud blaring sound or pattern of sounds) may be inconvenient to the user in the short-term, in the long-term it benefits the user by promoting behavior that reduces the likelihood of pressure ulcers.

While the alarm may continue, in some embodiments the audible alarm or other indication of the alarm may be silenced/deactivated by the user by performing a pressure release or by using the programming interface 304. If the user remains off the seat for the preset minimum release time, also known as a "full release duration," the alarm will be canceled, the indicator LED and the sit-time and release-time will reset, re-initialized, or altered. Other forms of user feedback, such as a display or vibrating motor can be used with, or in addition to, LEDs and a speaker.

In some embodiments, an optional accessory port 314 allows for other devices to be connected. These other devices may include, but are not limited to: alternative notification devices, such as a vibrating motor, amplified audible alarms, additional LEDs, or LCD monitor; data collection or logging devices; wireless transmitters that would send alarm notifications to a nurse or caregiver; or, other devices.

Figure 4:
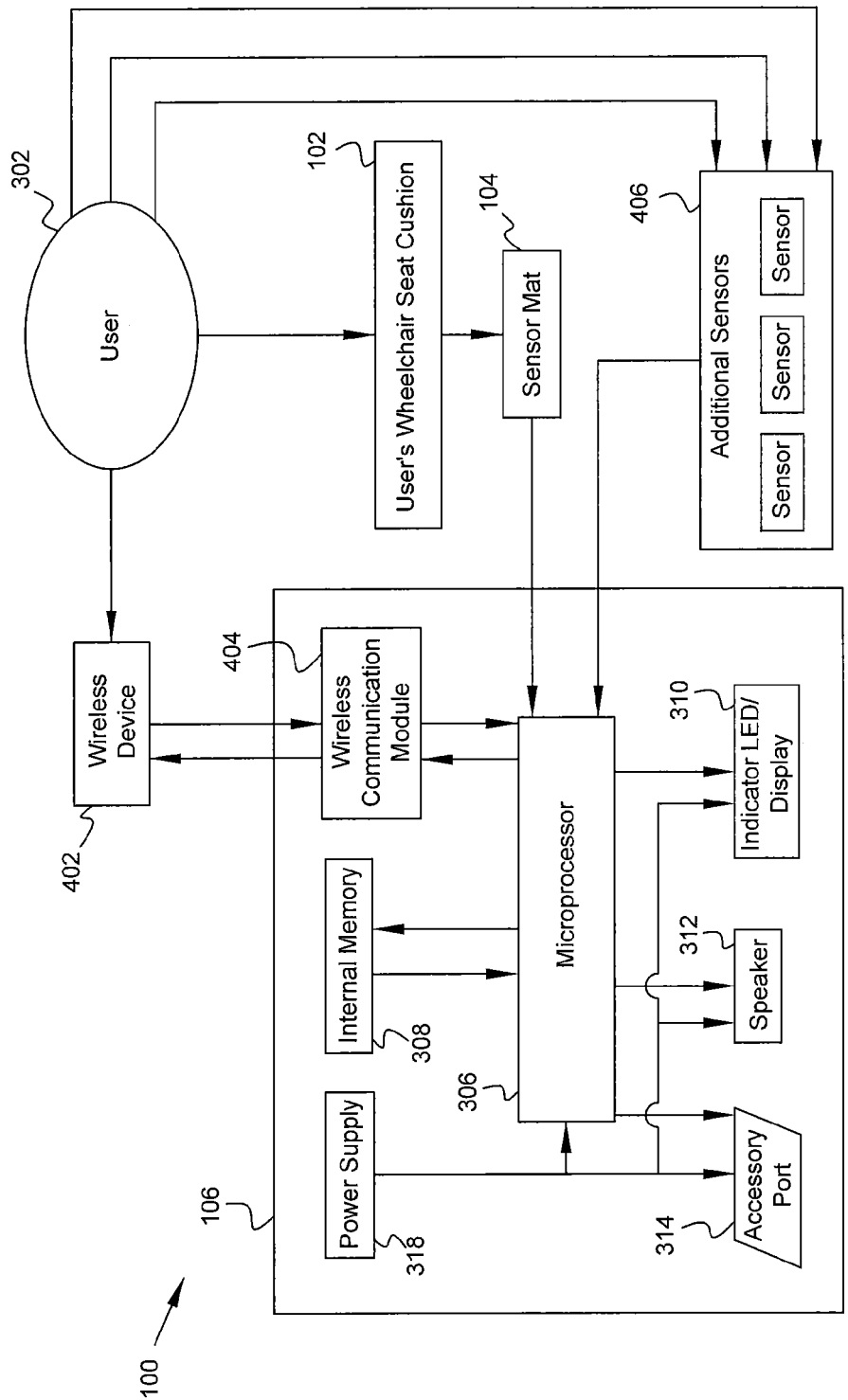
FIG. 4 is a system diagram of operable connections of the components of a pressure monitoring system in accordance with some embodiments of the present disclosure.

A system diagram of the operable connections between the components of a pressure monitoring system in accordance with some embodiments is shown in FIG. 4. This embodiment differs from that presented in FIG. 3 by the replacement of the programming interface 304 with the wireless device 402, the introduction of the wireless communications module 404 of the microprocessor unit 106 and the additional sensors 406. In some embodiments, the wireless device 402 may be a smart phone or smart watch used to monitor all connected sensors and provide detailed feedback to the user on its screen. For example, an iPhone, Apple Watch or Android Wear smart watch may be used. The user may also view data, including, but not limited to, current pressure values, historical values and statistics and battery levels. The user may make adjustments including, but not limited to, alarm settings, volume settings and timer limits. The wireless device may operate as and be separate from or in addition to the indicator LED or display 310. The user may enter his or her presets into the wireless device 402, such as a smartphone or smart watch. The user may also receive feedback from the system via the wireless device, such as alarms and sensor data.

The wireless communication module 404 enables communication between the wireless device 402 and the microprocessor 306.

The user may apply pressure to additional sensors 406 placed in pressure-sore-prone areas, such as the soles of shoes, armrest or the back of the chair of system 100. These additional sensors 406 send data to the microprocessor 306. The microprocessor receives the user's presets from the wireless communication module and stores it in internal memory, and receives pressure signals from the mat with electronic pressure sensor and additional sensors. The microprocessor calculates sit-time and time of pressure applied to the additional sensors and compares it to the user's presets stored in internal memory. It should be recognized that "sit-time" may refer to a period in which pressure is applied to a user's body above some threshold level whether that pressure is due to sitting in a wheelchair, lying on a bed, resting a foot or arm on a foot or arm rest, using crutches, leaning against a chair, or any other activity or configuration. Signals from the sensors 104, 406 are communicated back to the wireless device 402 via the wireless communication module 404. If the sit-time reaches the preset time limit a signal may be sent to the speaker 312, wireless device 402 and/or indicator 310. In some embodiments, the microprocessor 306 may also provide an output to a vibrating motor to provide indications of alarms or other status updates.

Figure 5:
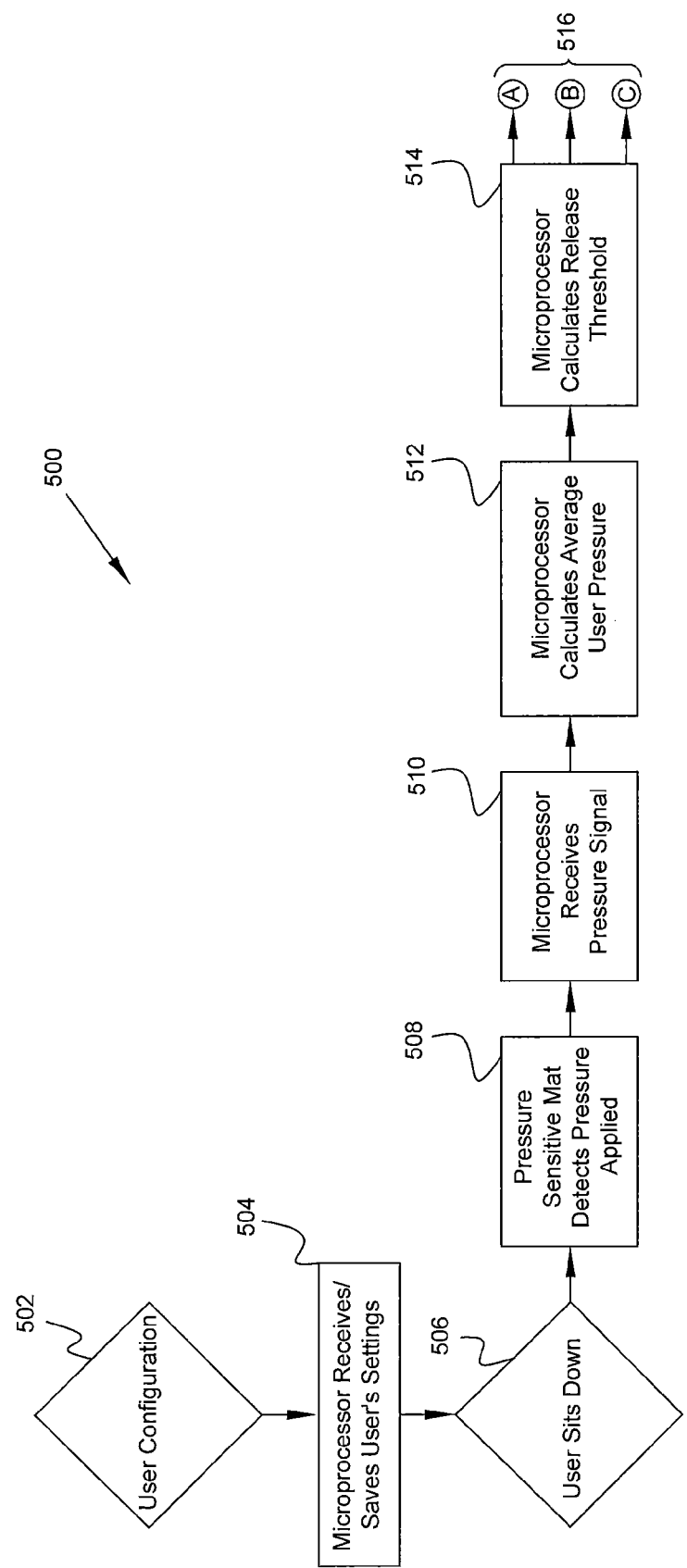
FIG. 5 is a flow diagram of the setup of a pressure monitoring system in accordance with some embodiments of the present disclosure.

FIG. 5 shows a flow diagram of the setup 500 of a pressure monitoring system. At block 502, the user chooses the system settings using the programming interface 304. The user may choose from settings such as: sit-time limit (the amount of time the user can sit (or apply a pressure greater than a threshold pressure to the sensor mat 104) before the alarm sounds (30 minutes, for example)); minimum release-time (the amount of time during which the user must release pressure less than a threshold in order to turn off the alarm and reset the sit-time (2 minutes, for example)); snooze enable (enables the ability to snooze (temporarily turn of the alarm) for a set period of time (5 minutes, for example)); "buy back" enable (allows the user to alter the sit-timer proportionate to the amount of time the user has performed a pressure release (for example, subtract 60 seconds of sit-time for every 4 seconds the user releases)); and sound enable (the user has the option to enable audible alarms or to use the device with only visual cues (LEDs or other displays)). Other possible settings may include selection of other methods for indicating an alarm such as a wireless notification or vibrating motor and administrator lock out to prevent a user from altering the system settings. At block 504, the settings are received by the microprocessor 306 and stored in the internal memory 308.

At block 506, the user sits down, causing the sensor mat 104 (or other pressure or force sensor) to detect and measure a pressure or force and output a signal to the microprocessor 306. The microprocessor 306 receives this signal at block 510. At blocks 512, the microprocessor 306 detects the user sitting (applying pressure) on the mat 104 and calculates the average pressure applied by the user, e.g., during an initial calibration interval. This average pressure may be by individual sensors or for the combination of sensors. An average pressure calculation is used to account for factors that may cause pressure readings to vary, such as changes in user weight, battery drainage, and shifting in the seat by the user during the initial calibration interval. At block 514, the microprocessor multiplies the average pressure by a threshold variable, e.g., between 70-90%, to calculate the release threshold. Finally, at block 516 the setup is complete and the system proceeds to A, B and/or C depending on the particular functionality selected by the user.

Figure 6:
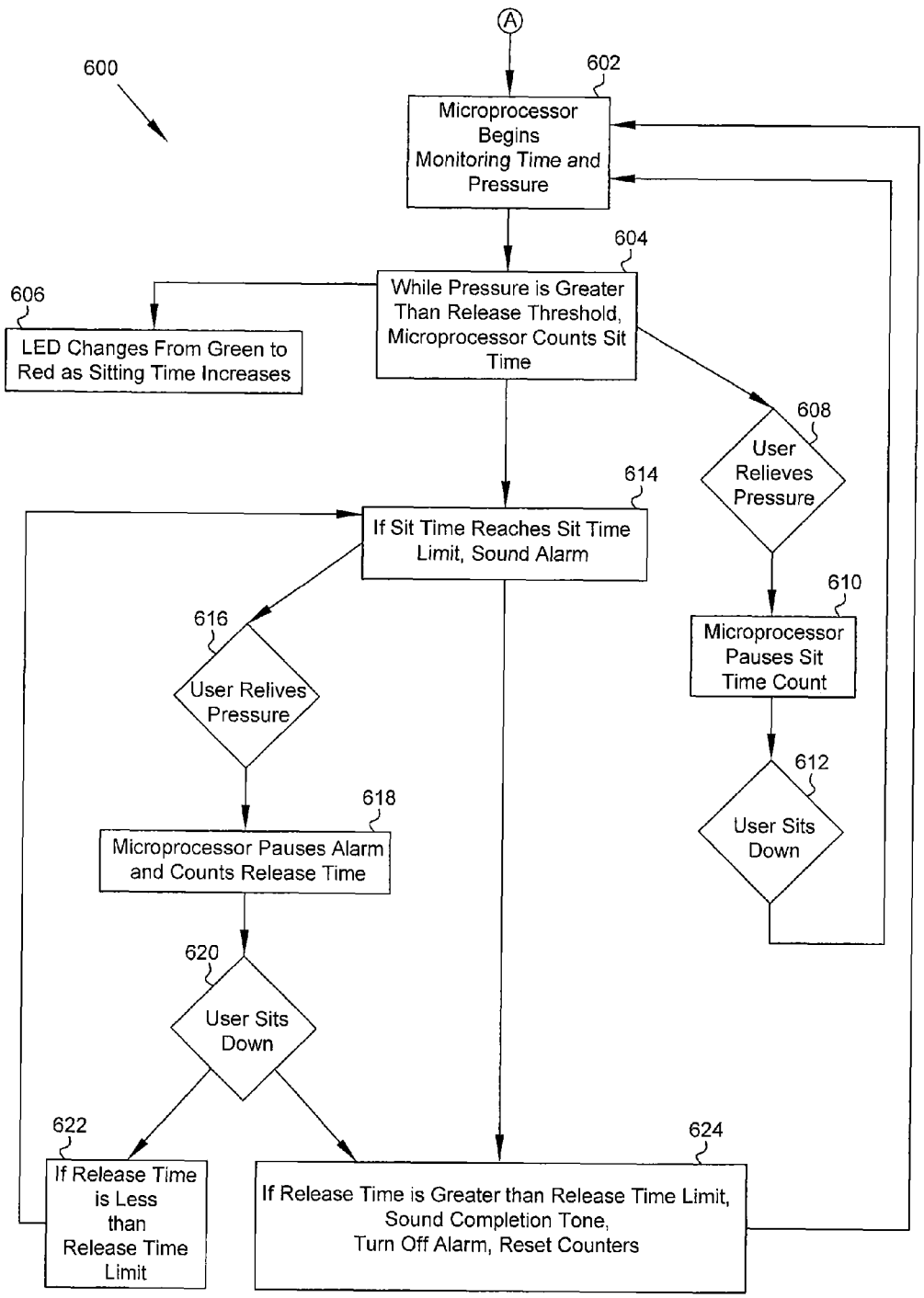
FIG. 6 is a flow diagram of the operation of a pressure monitoring system in accordance with some embodiments of the present disclosure.

FIG. 6 shows a flow diagram of the operation 600 of a pressure monitoring system in accordance with some embodiments. The operation 600 follows the above setup at A. At 602 the microprocessor 306 begins to monitor the applied pressure and time during which the pressure is applied. Next, while the pressure on the mat 104 is greater than the release threshold, the microprocessor 306 will run the sit-timer to keep track of how long the user's skin has been subjected to pressure greater than the release threshold. This may cause the LED or display 310 to provide an indication of the sit-timer status at 606. This may involve changing LED or display colors from green to red, including a pictorial version of a sand or digital timer, or display percentage of the sit-time limit used since the last pressure release. It should also be understood that these indications of the sit-timer status may also be audible sounds or physical vibrations.

If the user performs a pressure release at 608, in which the user reduces the pressure on the mat 104 below a release threshold, the microprocessor 306 will pause the sit-timer at 610. The sit-timer will remain paused at 610 until the user sits down which is detected by the mat 104 as a pressure rising above some threshold value. The process then returns to block 604.

When the sit-timer reaches the sit-time limit, the visual, audible and/or physical alarm is triggered at 614. The alarm will continue until the user performs a pressure release at 616. This pressure release causes, at 618, the microprocessor 306 to pause the alarm and to begin counting release time, or the time that detected pressure is less than the release threshold. At 620, the user sits down. If the measured release time is less than the release-time minimum, the process will return to block 614 and the sit-timer will not be reset. However, if the measured release-time is greater than the release-time minimum, a completion tone or visual or physical (such as a vibration) cue notifies the user, clears the alarm and resets the sit-time counter and release-time counter at block 624. The process then returns to block 602.

In some embodiments, two or more force or pressure sensors may be used. The microprocessor may be able to distinguish each signal individually and run separate sit timers, set sit-time limits, determine average and threshold pressures and sounds alarms for the sensors individually. The alarm may sound at the first instance of any sit timer reaching a sit time limit and may include an additional sound if another sit timer for another sensor reaches the sit-time limit. In some embodiments, each sensor may have a unique alarm such that the user is better informed which sensor has triggered a given alarm event. The alarms may also be communicated with visual, physical or other indications. In some embodiments, a representation of the user's body is displayed on a display, and an indication of each sensor (e.g., a first sensor and a second sensor) is displayed in relation to the body. The indication of each sensor may be color-coded based on a status of the corresponding sit timer.

In some embodiments, a "snooze" method for delaying pressure releases is disclosed. This method comprises a way to temporarily extend a user's sit-time and delaying the required full pressure release while still requiring the user to momentarily shift the pressure applied. When a user has reached the programmed sit-time limit and has triggered the alarm, it can be turned off temporarily, or snoozed, by releasing pressure for a few seconds. This will temporarily extend the user's allotted sit-time.

Figure 7:
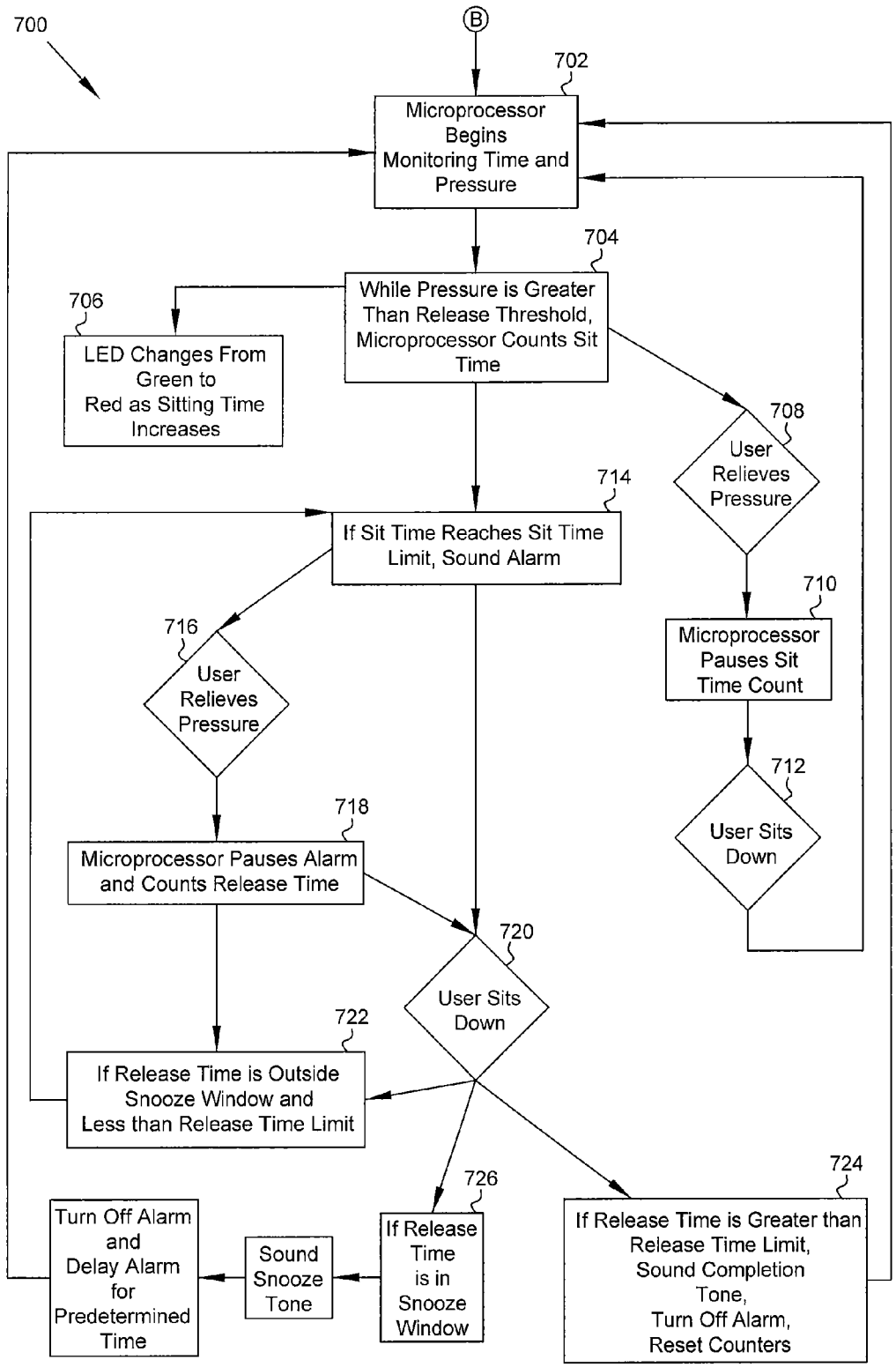
FIG. 7 is a flow diagram of the operation of a pressure monitoring system using a snooze feature in accordance with some embodiments of the present disclosure.

FIG. 7 shows a flow diagram of the operation 700 of a pressure monitoring system in accordance with some embodiments. In the embodiment of FIG. 7, the user has selected to enable the snooze feature of the present disclosure. In some embodiments, the snooze is activated with pressure releases. This method comprises a way to temporarily extend a user's sit-time and delaying the required pressure release for the pressure release time minimum, while still requiring the user to momentarily release the pressure applied. When a user has reached the programmed sit-time limit and has triggered the alarm, the alarm can be turned off or delayed temporarily (snoozed) by releasing pressure for a few seconds. This snooze feature may be activated by releasing pressure for some period less than a full release procedure. In some embodiments, the snooze feature is activated by releasing pressure for a few seconds within a "snooze window" of, for example, between 3 and 10 seconds. The snooze window may comprise a period of time, for example, 3 to 10 seconds following an event. This event could be the triggering of an alarm or may occur when the user begins a release event.

The snooze feature may include the ability to extend the alarm by the same time as that found by multiplying the snooze-enabling pressure release time by the buy-back ratio (discussed below) and/or a fixed period of time. In some embodiments, the extension of an alarm may be by a fixed period of time which is reduced for each subsequent snooze activated by the user of that alarm, thereby discouraging the user from snoozing excessively.

The system may provide audio, visual or other indicators as to the status of the snooze function to inform the user when snooze is available. For instance, at the start of a snooze window the system may provide an indication such that the user is aware that sitting down will trigger the snooze function. The system may also provide a second indication at the conclusion of the snooze window. At this point the user can choose to either complete a full pressure release to reset the sit-timer or sit down at which point the alarm will sound again. In some embodiments, the system will provide an indication when the user has performed a pressure release greater than the minimum release time such that the user is aware that sitting down at any time will cause the sit-timer to reset.

The operation 700 begins at B and proceeds to 702. Blocks 702 to 720 may proceed similarly to blocks 602-620 from FIG. 6. At block 720 an alarm has sounded, may have been temporarily silenced, release time measured and the user sat down. At this point the process may proceed in three different manners. First, at block 722 the user's measured release time does not fall within the snooze window and is less than the release time minimum. This will cause the process to return to block 714. Second, the user may perform a pressure release longer than the pressure release time minimum at block 724. A competition indication may be provided and the sit-timer reset before the process returns to block 702.

Finally, the process may proceed to block 726, at which the user sits back down within the snooze window such that the pressure release threshold is crossed. A tone may be sounded indicating that the snooze feature has been enabled which delays the resounding of the alarm for some predetermined period of time, for example, by five minutes. In some embodiments, the use of a snooze feature may shorten a subsequent sit-time limit and/or require a longer pressure release procedure.

Figure 10A:
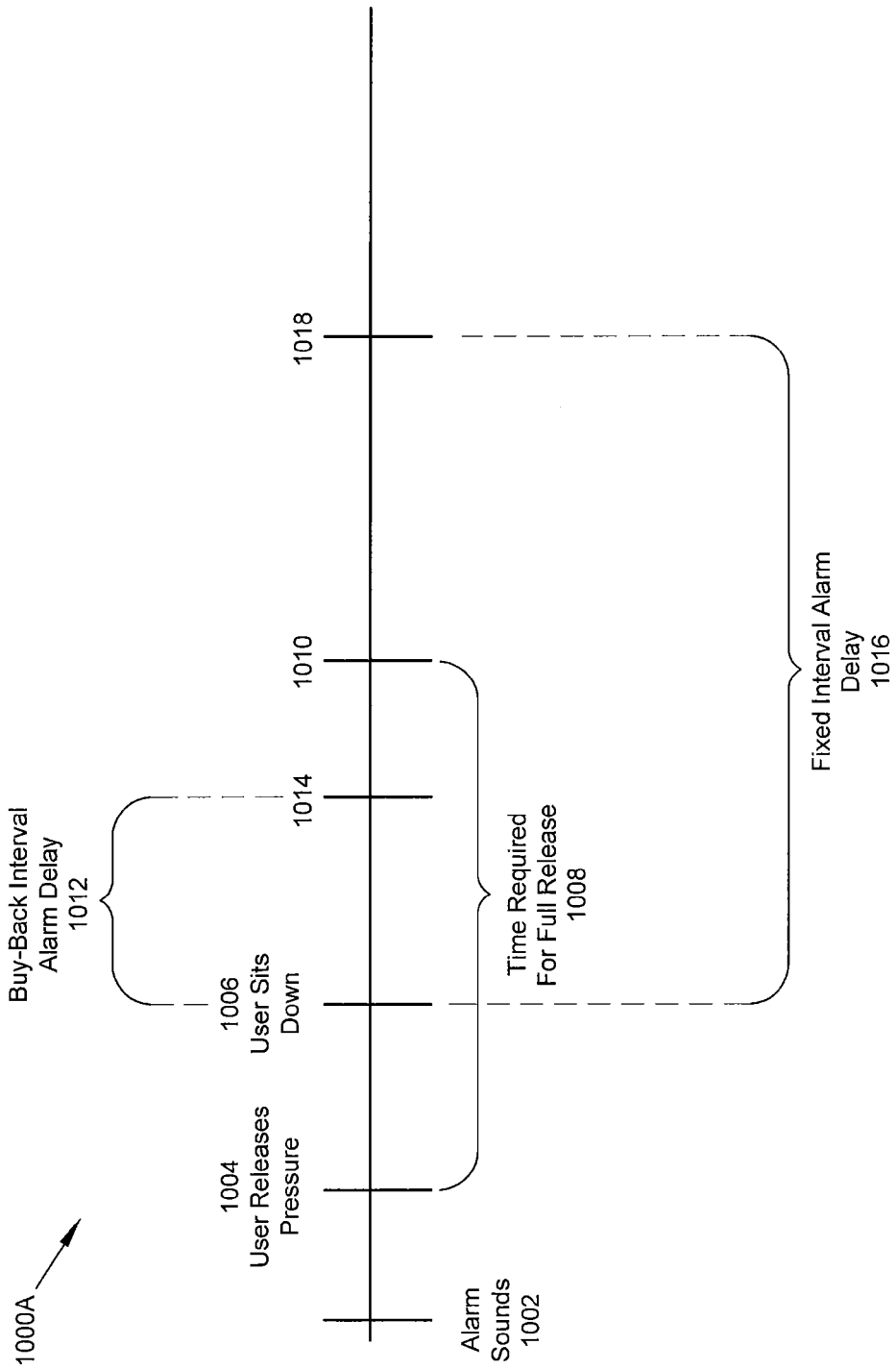
FIGS. 10A and 10B illustrate a timeline of the snooze feature in accordance with some embodiments of the present disclosure.
Figure 10B:
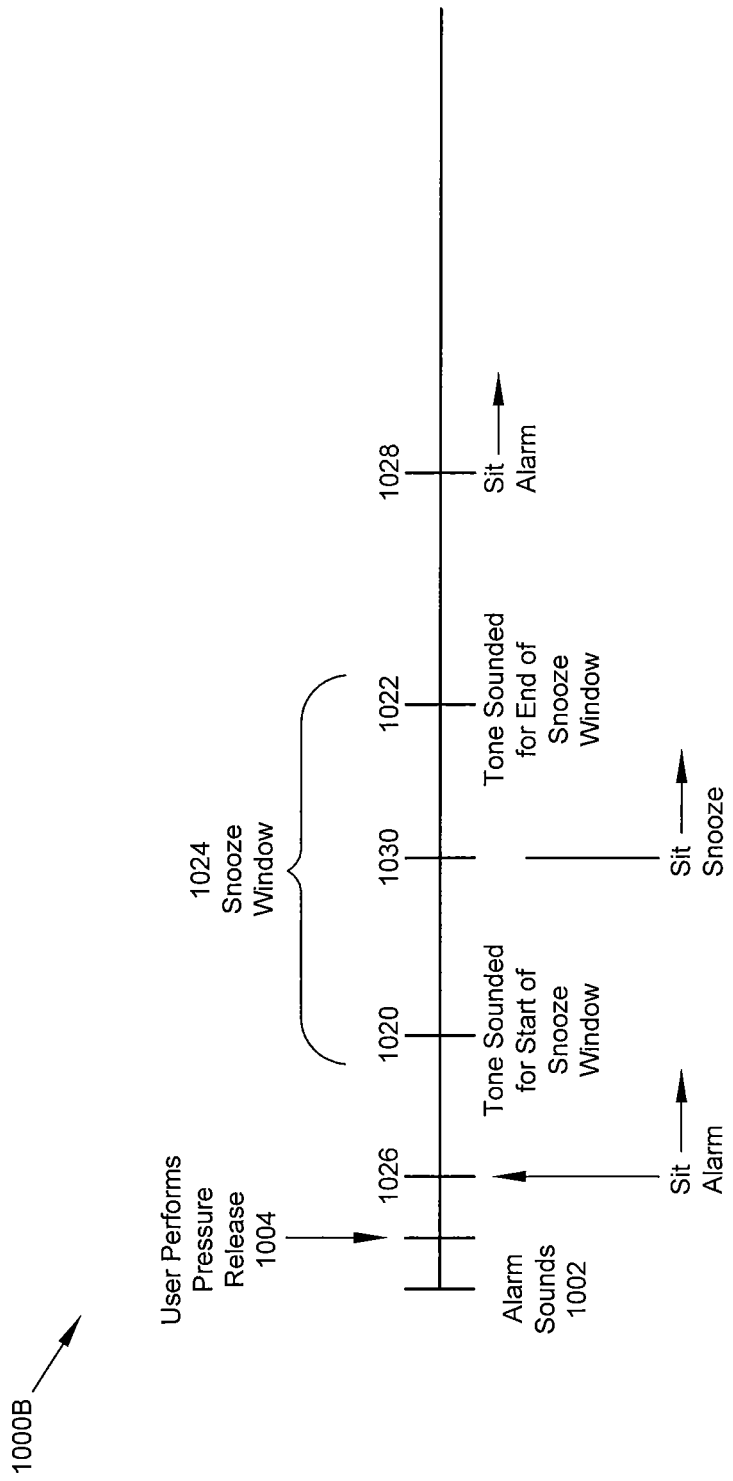

FIGS. 10A and 10B illustrate timelines 1000A and 1000B of the snooze feature in accordance with some embodiments. With reference to FIG. 10A, an alarm sounds or blares at 1002 when the sit-timer reaches the sit time limit. At a point in time 1004, the user initiates a pressure release which occurs until point 1006, at which time the user sits down, placing a pressure on the sensor mat greater than the threshold pressure. The duration 1008 from time 1004 to 1010 corresponds to a full release (e.g., 2 minutes). If the user sits down after time 1010 (such a sitting down is not shown in FIG. 10A), the alarm is cleared and the sit-timer is reset. In some embodiments, if the user sits down (i.e., ends the pressure release event) at any point in time between 1004 and 1010, the user activates the snooze feature. In some embodiments, the snooze feature will delay the re-sounding of the alarm proportionally to the time the user has released pressure, as represented by 1012. This proportion may be equal to the buy-back ratio discussed below, or may be another predetermined proportion. As a result, the re-sounding of the alarm is delayed until 1014. In some embodiments, the release procedure may result in delaying the alarm by a fixed amount 1016 (instead of a proportional delay) such that the alarm will re-sound at point 1018. The delays 1016 and 1012, respectively, may be any amount as programmed by the user, and one need not necessarily be longer than the other.

FIG. 10B illustrates a timeline 1000B of the snooze feature in accordance with some embodiments. Here, the user is required to sit back down (or, increase the pressure on the mat above some threshold value) within a specific time window (referred to as a snooze window) in order to snooze. The snooze window may be relative to the blaring of the alarm or relative to the start of the pressure release. The use of a snooze window better ensures that the activation of the snooze feature when it is intended by the user. At a point in time 1002 an alarm is sounded when the sit-timer reaches a sit-time limit. The user subsequently performs a pressure release (beginning at time 1004), during which time the alarm is silenced. If the user were to sit down at point 1026, before the start of snooze window 1024, the alarm would sound again. At time 1020 a tone or other indication is sounded (or displayed visually or via vibration, etc.) informing the user of the start of the snooze window. If the user sits down at point 1030 the snooze feature will be activated because this occurs within the snooze window 1024. If the user maintains the pressure release to point 1022, the user will receive an indication that the snooze window has closed (ended). Sitting down at point 1028 (which is after the end of the snooze window) will then trigger the alarm unless the duration of the release event is equal to or longer than the full release duration (minimum release time; this may be 2 minutes, for example).

Figure 8:
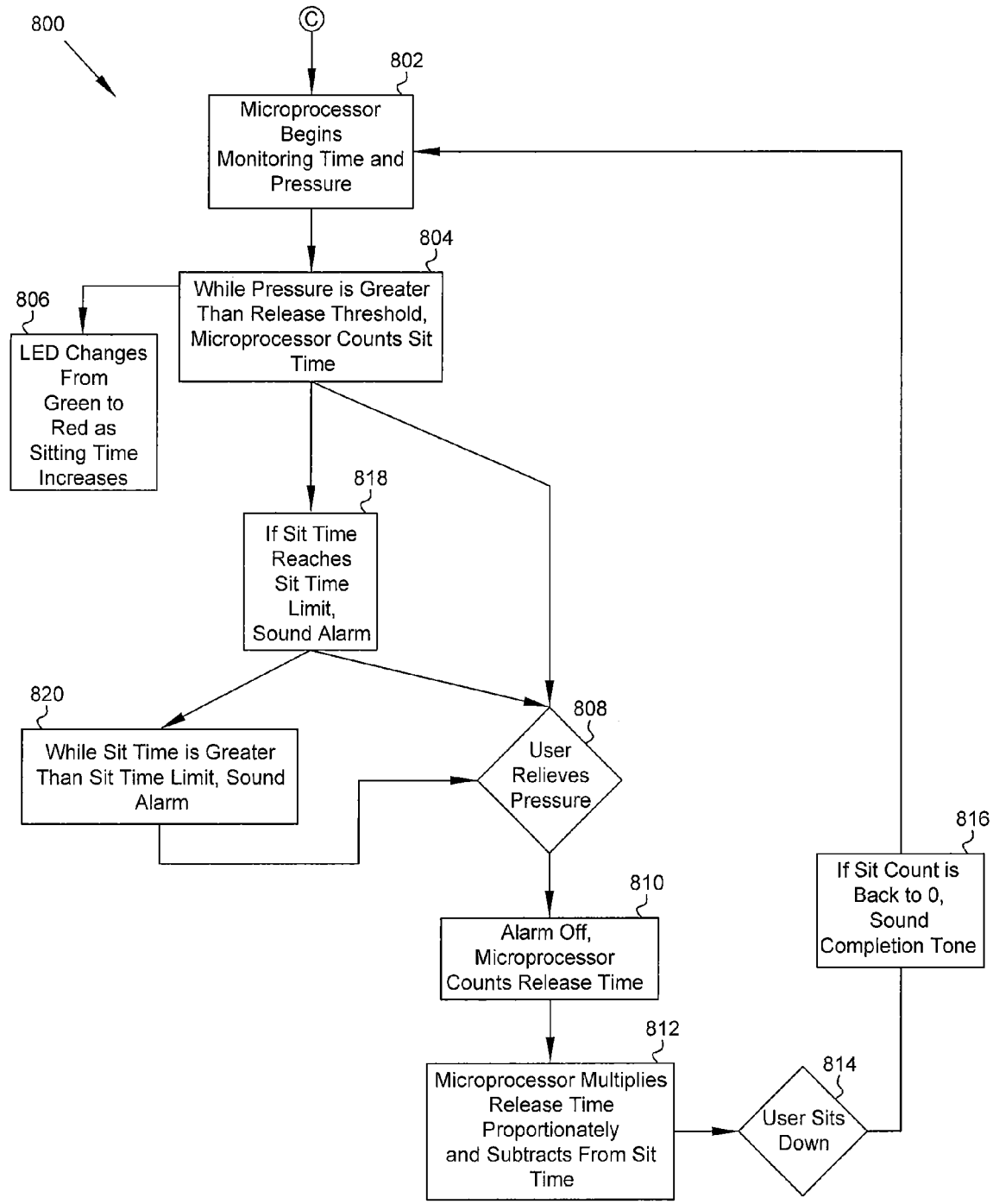
FIG. 8 is a flow diagram of the operation of a pressure monitoring system using a buyback feature in accordance with some embodiments of the present disclosure.

FIG. 8 shows a flow diagram the operation 800 of a pressure monitoring system using a buy-back feature. In some embodiments, the "buy-back" feature or method alters the sit-time limit or the sit-timer based on a pressure release event. This method may comprise taking the preset sit-time and dividing it into the preset release duration to get a buy-back ratio. As a user exerts pressure on mat 104 greater than the release pressure, the microprocessor 306 tracks the amount of sitting time. For example, for every second of time the user spends off of the seat, as detected by the mat 104 as pressure below the release threshold, the user "buys back" time. This buy-back time may be subtracted from the user's accumulated sit-time. For example, if the preset release duration is 2 minutes and the sit-time preset is 30 minutes, the buy-back ratio is 1:15. Thus, when the buy-back option is enabled, every second that the user is not applying pressure greater than the release threshold deducts 15 seconds from his/her accumulated sit-time. This feature allows the user to avoid alarms by releasing pressure intermittently. This encourages the user to get in the habit of regular, albeit spontaneous, shifting of his or her weight much as able-bodied persons do subconsciously when sitting.

As another example, a user who releases pressure at any time may "buy back" sitting time. The term "buy back" is suggestive of the incentive provided to the user. In particular, by performing a pressure release (something which the user might not otherwise do), the user is essentially buying something that is beneficial to the user—postponement of the sounding of an alarm. In some embodiments, if a user has been sitting for 10 minutes (which is less than, e.g., the alarm limit of 30 minutes, such that the alarm has not sounded yet) and performs a pressure release for 4 seconds, the monitoring device, using a 1:15 buy-back ratio, will credit back to the user 4*15=60 seconds of sitting time. This adjusts the user's accumulated sitting time (sit-timer) to 9 minutes.

If the user performs another pressure release for 8 more seconds, the monitoring device would credit the user with another 2 minutes (8*15=120 seconds), adjusting the user's accumulated sitting time to 7 minutes. This technique encourages the user to do regular, spontaneous pressure releases, and provides a way for the user to avoid the alarm while achieving the ultimate goal (from the perspective of the user's health) of preventing pressure ulcers.

In some embodiments, the buy-back time is not subtracted from the sit-timer; rather, the sit-time limit is extended by an amount equal to the buy-back time. One way to think of this is that a runner in a race can run in reverse, or the finish line can be pushed back, and either action will cause the runner to take longer to reach the finish line (similar to the alarm sounding). This extension may only affect the sit-time limit for the current sit-timer and not subsequent sit-time limits after a full pressure release has been performed. In some embodiments, a user may be able to buy-back more time than the sit-time limit by performing a pressure release longer than that required for a full release. The delay in a subsequent sit-time limit may be equal to the time spent performing the pressure release longer than a full release multiplied by the buy-back ratio.

The process in FIG. 8 starts at C. Blocks 802 to 810 of FIG. 8 are performed in a manner similar to blocks 602-610 of FIG. 6. At block 812, if the release time is less than the release time minimum to reset the sit-timer, the microprocessor 306 multiples the release time by the buy-back ratio and alters the sit-timer or sit-time limit as described above. If the release time is greater than the minimum release time, the microprocessor may set the sit-timer back to zero and provide a sound, visual or other physical indication the counter has been reset. The process then returns to block 802.

When the sit-timer reaches the sit-time at 818 limit the system will sound the alarm audibly, visually or with some other physical indication. The alarm will continue at 820 until the user performs a pressure release at block 808.

One of ordinary skill in the art will recognize that the features and operations disclosed in FIGS. 5 to 8 may be combined with one another or altered in order to provide the functionality required by a specific user.

Figure 9A:
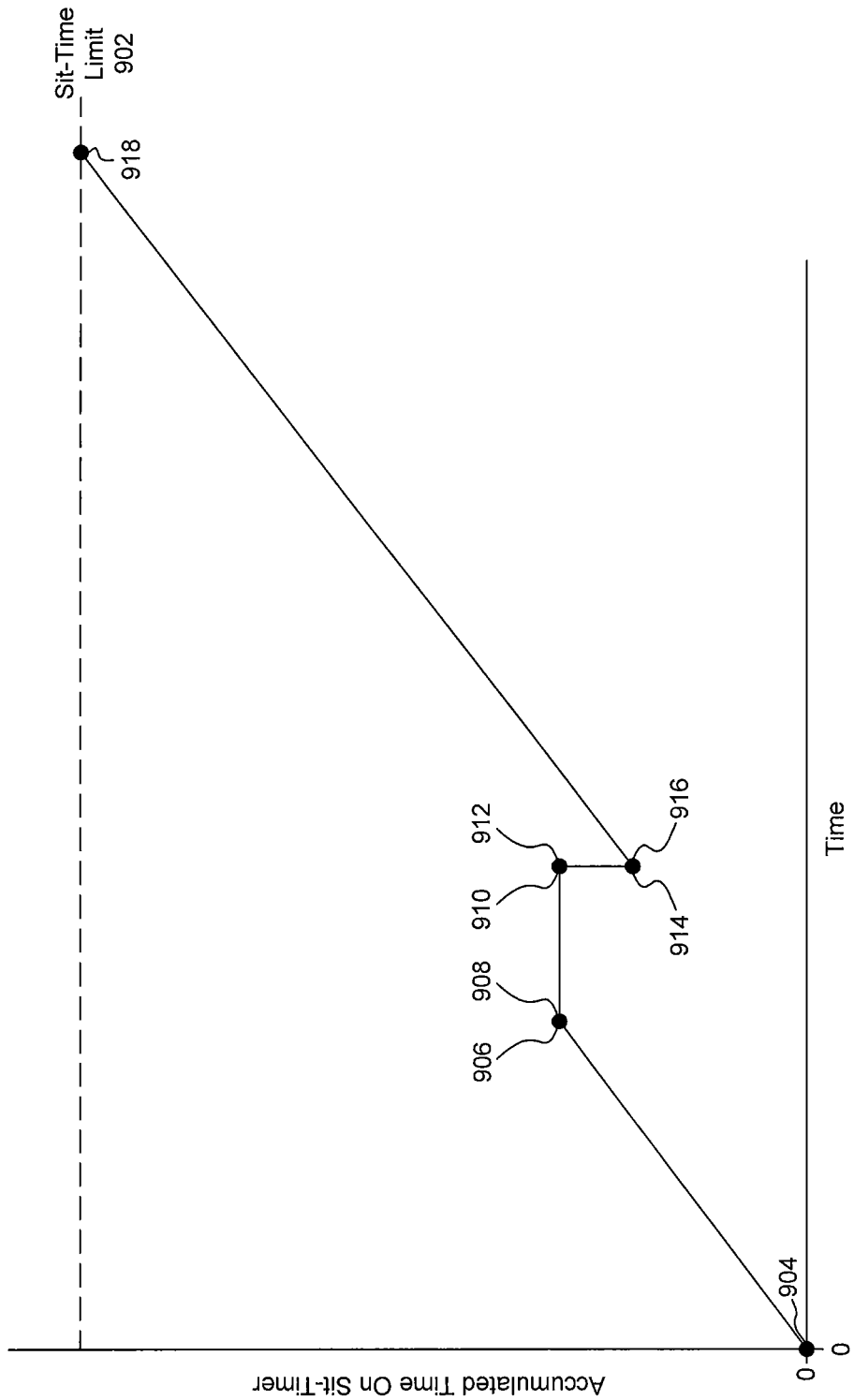
FIGS. 9A and 9B are graphs of alterations to a sit-timer and sit-time limits in accordance with some embodiments of the present disclosure.
Figure 9B:
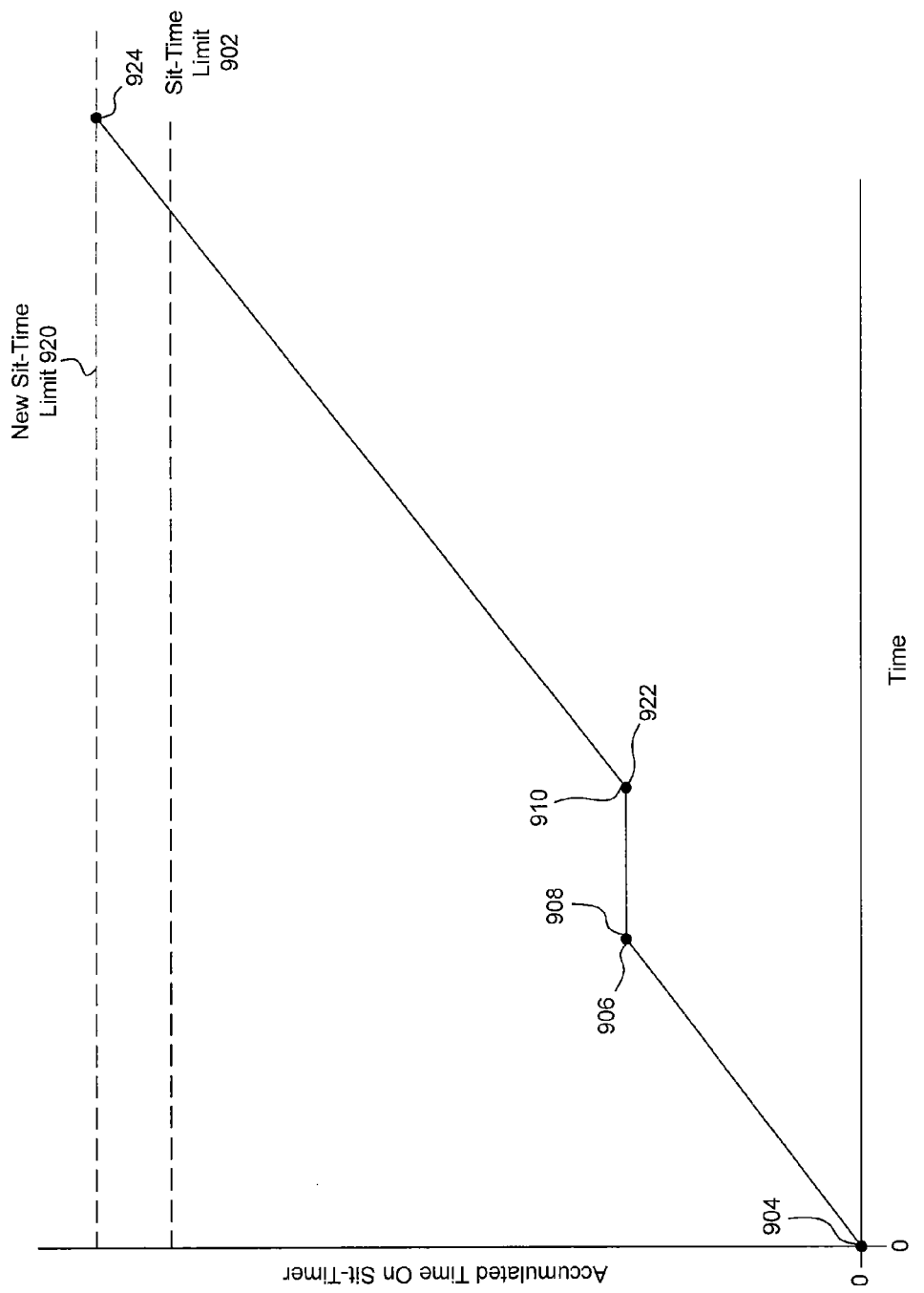

FIGS. 9A and 9B show embodiments involving alterations to the sit-timer and sit-time limit, respectively, resulting from a pressure-releasing, buy-back event. With reference to FIG. 9A, the alterations begins at time 0 with an original sit-time limit set at 902, which may be a sit-time limit as programmed by the user. The user is initially sitting (i.e., no pressure release) from points in time 904 to 906, wherein this sitting is detected by the sensor mat 104 as being greater than a predetermined threshold pressure. At point 906 the user performs a pressure release lasting from points 908-910. This pressure release may be less than the minimum release time (e.g., 2 minutes) required to reset the sit timer, and therefore results in a buy-back of time, delaying the time until the sit timer reaches the sit time limit 902. In order to delay the time until the sit time limit 902 is reached, the buy-back time is subtracted from the user sit timer. With a 1:15 buy-back ratio, for example, a pressure release of 4 seconds would result in a buy-back time of 60 seconds which is subtracted from the user sit timer. The buy-back time is represented as the vertical distance between points 912 and 914. When the user sits back down, at point 916, the sit-timer resumes running from its new, lower value until reaching the sit-time limit at point 918.

In some embodiments, the sit-time limit 902 (as opposed to the sit-timer) may be altered such that a buy-back results in a delay until the sit-time limit is reached. This embodiment is shown in FIG. 9B, in which functionality corresponding to points in time 904, 906, 908, and 910 is the same as in FIG. 9A. Referring to FIG. 9B, instead of subtracting time from the user's sit-timer, the buyback performed from 908 to 910 will result in shifting the sit time limit from 902 to 920. The user resumes sitting (ends the release event) at point 922 and the sit timer runs until hitting the new sit time limit 920 at point 924. In this embodiment, the alarm time (sit time limit) is pushed back by an amount equal to the buy-back time, but in other embodiments, the alarm time may be pushed back by a different amount.

Figure 11:
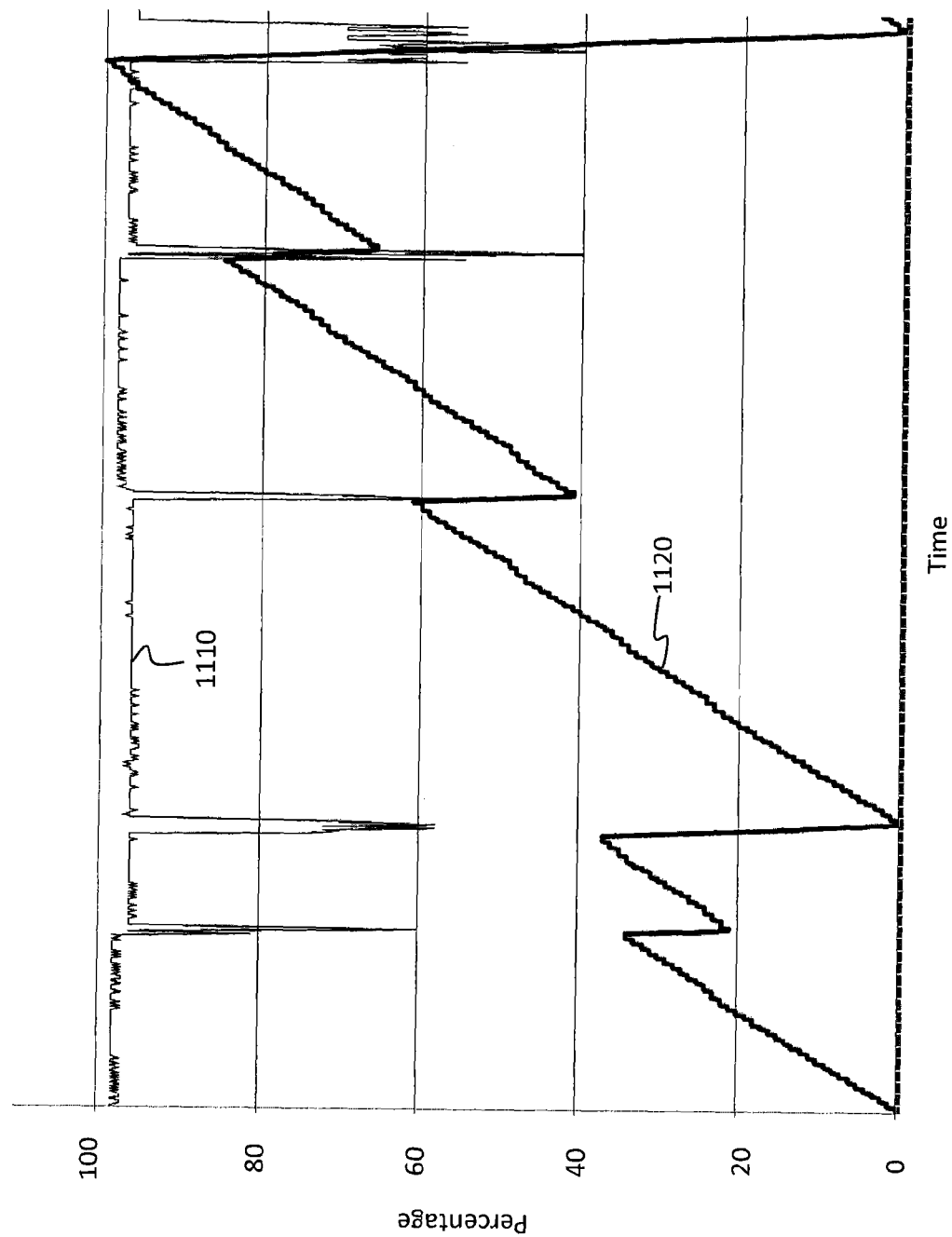
FIG. 11 illustrates test data regarding modifying a sit-timer in accordance with some embodiments of the present disclosure.

FIG. 11 illustrates test data regarding modifying a sit-timer in accordance with some embodiments of the present disclosure. Similar to FIG. 9A, the horizontal axis in FIG. 11 depicts time. Plot 1110 is a sensor signal, e.g., from a pressure or force sensor, and plot 1120 is accumulated time on the sit-timer, and these quantities are plotted as a function of time. The vertical axis in FIG. 11 depicts percentage. In the context of plot 1110, the depicted percentage is percentage of the average value (average value was previously determined in the initial calibration period). In the context of plot 1120, the depicted percentage is percentage of the sit time limit (e.g., percentage of progress up to 30 minutes, if the sit time limit is set to 30 minutes).

FIG. 11 shows actual test data based on a user using the pressure relief compliance system for about 45 minutes. In this example, a single pressure release threshold of 75% (of average pressure) was used. Thus, at points in time when signal 1110 falls below 75%, a pressure release is initiated, and when the signal 1110 returns above 75%, the pressure release is ended, and the sit-timer 1120 is modified (here, reduced) in proportion to the duration of the pressure release. Several pressure release events are seen in FIG. 11, and for each of these pressure releases the user is "rewarded" in the sense that the alarm is postponed in proportion to the pressure release.

Near the right hand side of FIG. 11, the sit-timer finally reaches 100% of the sit time limit, at which time the alarm sounds. FIG. 11 shows that the user performed a pressure release soon after the sit time limit was reached, and after the pressure release (which was a full pressure release, i.e., of duration at least equal to the predetermined full release threshold), the sit-timer was resetted (here, to 0). FIG. 11 demonstrates, among other things, the benefit of initially calculating an average pressure, because the measured pressure is observed to fluctuate as shown by plot 1110.

In some embodiments, the user is not able to buy back more than sit-time limit. In such embodiments, the buy-back functionality essentially saturates at a maximum (the sit-time limit) such that no matter how many pressure releases the user performs and no matter how long such releases last, the user still needs to perform under release in the next 30 minutes (for example), consistent with the goal of preventing a long period of time to ensue without a pressure release.

In some embodiments, the injury preventing limits and monitoring of the present disclosure is used to prevent and minimize injuries resulting from other conditions. For example, a blood flow monitoring system may be used to indicate the time at which an appendage must be moved in order to provide the necessary circulation to that appendage. Such a system may use a sensor which monitors blood flow directly, or the sensors may indicate a condition or event which is indicative of the blood flow. For instance, a pressure or force sensor could be used to indicate that the appendage has remained in a stationary position beyond some limit and, therefore, that the appendage needs to be moved to provide necessary blood circulation.

In some embodiments, a pressure sensor could be used to indicate the pressure of or within a particular part of the body. For example, a bladder pressure sensor could provide a user indication of when a bladder is full to prevent the bladder from filling up to the kidneys which presents a stroke hazard.

In some embodiments, a user or caregiver may disable the ability to turn off the device or mute the alarm in order to ensure compliance. Alternatively, where the circumstances do not readily allow the user to perform a pressure release for the minimum release time, the pressure relief reminder system may allow the user to delay (snooze) the alarm, while still relieving pressure momentarily.

The present disclosure provides a pressure relief reminder system and methods for assisting a user in the development of healthy long-term pressure release habits through the reminder and compliance incentives provided by the disclosed use of a pressure or sensor mat connected to a microprocessor. In some embodiments the user is able to snooze and/or buy-back time by performing pressure releases less than some minimum pressure release time. This will help train the user to shift weight and perform pressure releases regularly. Ultimately, users will develop habits that facilitate regular pressure releases without reliance on an alarm.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a computer readable medium. The computer readable medium can be a machine-readable storage device, a machine-readable storage substrate, a memory device, or a combination of one or more of them.

The term "processor" encompasses all apparatus, devices, and machines for processing data, including by way of example a programmable processor, a computer, or multiple processors or computers. The processor can include, in addition to hardware, code that creates an execution environment for the computer program in question, e.g., code that constitutes processor firmware, a protocol stack, a database management system, an operating system, or a combination of one or more of them.

A computer program (also known as a program, software, software application, app, script, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network or as an app on a mobile device such as a tablet, Phablet, PDA, smartphone, or wearable technology The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer or mobile device, smartphone or tablet. Generally, a processor will receive instructions and data from a read only memory or a random access memory or both. The essential elements of a computer are a processor for performing instructions and one or more data memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a mobile smartphone, a personal digital assistant (PDA), tablet, a mobile audio or video player, a game console, a Global Positioning System (GPS) receiver, to name just a few.

Computer readable media suitable for storing computer program instructions and data include all forms data memory including non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube), LCD (liquid crystal display) monitor or other monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

Although examples are illustrated and described herein, embodiments are nevertheless not limited to the details shown, since various modifications and structural changes may be made therein by those of ordinary skill within the scope and range of equivalents of the claims.

I claim:

1. A system comprising:
   at least one sensor capable of measuring force or pressure applied by a portion of the body of a user;
   a speaker;
   a memory;
   a processor operably coupled to receive force or pressure measurements from the at least one sensor, the processor programmed to:
      initialize a sit timer in the memory;
      run the sit timer while the force or pressure measured by the at least one sensor is greater than a release threshold;
      cause the speaker to sound an alarm in an event the sit timer reaches a predetermined sit time limit before the user performs a release having a predetermined full release duration;
      detect a release event occurring after the sit timer reaches the sit time limit, wherein the measured force or pressure is less than the release threshold during the release event;
      cause the speaker to silence the alarm in response to the detected release event; and
      in response to the detected release event, provide the user additional time until the alarm is next sounded,
   wherein the processor is further programmed to provide the user a fixed amount of additional time until the alarm is next sounded, if the release event is shorter than the predetermined full release duration.

2. The system of claim 1, further comprising a display element configured to provide a visual indication of a status of the sit timer.

3. The system of claim 1, further comprising a motor configured to cause a vibration in an event the sit timer reaches the sit time limit.

4. The system of claim 1, further comprising a wireless transmitter capable of wireless transmitting a signal in an event the sit timer reaches the sit time limit.

5. The system of claim 1, wherein the at least one sensor includes a first sensor and a second sensor, and the processor is programmed to update respective sit timers corresponding to the first and second sensors and cause the speaker to sound the alarm in an event that either sit timer reaches the sit time limit.

6. A system comprising:
at least one sensor capable of measuring force or pressure applied by a portion of the body of a user;
a speaker;
a memory;
a processor operably coupled to receive force or pressure measurements from the at least one sensor, the processor programmed to:
initialize a sit timer in the memory;
run the sit timer while the force or pressure measured by the at least one sensor is greater than a release threshold;
cause the speaker to sound an alarm in an event the sit timer reaches a predetermined sit time limit before the user performs a release having a predetermined full release duration;
detect a release event occurring after the sit timer reaches the sit time limit, wherein the measured force or pressure is less than the release threshold during the release event;
cause the speaker to silence the alarm in response to the detected release event; and
in response to the detected release event, provide the user additional time until the alarm is next sounded,
wherein the processor is programmed to provide the user the additional time until the alarm is next sounded only if the release event has a duration within a predetermined range.

7. The system of claim 6, wherein the amount of additional time provided to the user until the alarm is sounded is based on a duration of the release event.

8. The system of claim 6, wherein the processor is further programmed to cause the speaker or a display element to output an audible or visual indication, respectively, at the start of the predetermined range following the start of the release event.

9. The system of claim 6, wherein the processor is further programmed to cause the speaker or a display element to output an audible or visual indication, respectively, upon the end of the release event if the duration of the release event is within the predetermined range.

10. The system of claim 6, wherein the processor is further programmed to cause the speaker or a display element to output an audible or visual indication, respectively, upon the end of the predetermined range following the start of the release event.

11. The system of claim 6, wherein the processor is further programmed to cause the speaker to sound the alarm if the duration of the release event is greater than an upper limit of the predetermined range and lower than the predetermined full release duration.

12. A method comprising:
with at least one sensor, measuring force or pressure applied by a portion of the body of a user;
initializing a sit timer in a memory;
running the sit timer while the force or pressure measured by the at least one sensor is greater than a release threshold;
sounding an alarm in an event the sit timer reaches a predetermined sit time limit before the user performs a release having a predetermined full release duration;
detecting a release event occurring after the sit timer reaches the sit time limit, wherein the measured force or pressure is less than the release threshold during the release event;
silencing the alarm in response to the detected release event; and
in response to the detected release event, providing the user additional time until the alarm is next sounded,
wherein providing the user additional time comprises providing the user a fixed amount of additional time until the alarm is next sounded, if the release event is shorter than the predetermined full release duration.

13. The method of claim 12, further comprising displaying a visual indication of a status of the sit timer.

14. The method of claim 12, further comprising operating a motor to cause a vibration in an event the sit timer reaches the sit time limit.

15. The method of claim 12, further comprising wirelessly transmitting a signal in an event the sit timer reaches the sit time limit.

16. The method of claim 12, wherein the at least one sensor includes a first sensor and a second sensor, the method comprising updating respective sit timers corresponding to the first and second sensors and sounding the alarm in an event that either sit timer reaches the sit time limit.

17. The method of claim 16, the method further comprising:
displaying a representation of the body of the user; and
displaying an indication of the first and second sensors in relation to the body, the indication of each of the first and second sensors being color-coded based on a status of the corresponding sit timer.

18. A method comprising:
with at least one sensor, measuring force or pressure applied by a portion of the body of a user;
initializing a sit timer in a memory;
running the sit timer while the force or pressure measured by the at least one sensor is greater than a release threshold;
sounding an alarm in an event the sit timer reaches a predetermined sit time limit before the user performs a release having a predetermined full release duration;
detecting a release event occurring after the sit timer reaches the sit time limit, wherein the measured force or pressure is less than the release threshold during the release event;
silencing the alarm in response to the detected release event; and
in response to the detected release event, providing the user additional time until the alarm is next sounded,
wherein the user is provided additional time only if the release event has a duration within a predetermined range.

19. The method of claim 18, further comprising outputting an audible or visual indication at the start of the predetermined range following the start of the release event.

20. The method of claim 18, further comprising outputting an audible or visual indication upon the end of the release event if the duration of the release event is within the predetermined range.

21. The method of claim 18, further comprising outputting an audible or visual indication upon the end of the predetermined range following the start of the release event.

22. The method of claim 18, further comprising sounding the alarm if the duration of the release event is greater than an upper limit of the predetermined range and lower than the predetermined full release duration.

23. The method of claim 18, wherein the amount of additional time provided to the user until the alarm is sounded based on a duration of the release event.

24. The method of claim 23, wherein the additional time is a predetermined multiple of the duration of the release event.

25. A system comprising:
a sensor capable of measuring a force or pressure applied by a portion of a user's body;
an alarm device;
a memory device capable of storing a first time duration value;
a processor operably connected to said sensor, said memory, and said alarm device, wherein said processor receives from said sensor a sensor signal representative of the measured force or pressure, and wherein said processor is programmed to:
initialize a sit timer;
run the sit timer while the sensor signal is greater than a first threshold;
determine, for the condition where the sit timer has run for a time less than the first time duration value, a release event, wherein the release event has a release event duration which begins when the sensor signal is less than a second threshold and ends when the sensor signal is greater than the first threshold;
calculate a time duration offset as a function of the release event duration;
calculate a second time duration value from the first time duration value and the time duration offset; and
send an alarm signal to said alarm device for the condition where:
no release event was determined and the sit timer runs for a time not less than the first time duration value, or
a release event was determined and the sit timer runs for a time not less than the second time duration,
wherein said alarm device activates an alarm upon receipt of the alarm signal.

26. The system of claim 25, wherein the time duration offset is a predetermined multiple of the duration of the first release event.

27. The system of claim 25, wherein the processor is further programmed to:
detect a second release event occurring after the alarm signal is sent, wherein the second release event has a release event duration which begins when the sensor signal is less than the second threshold and ends when the sensor signal is greater than the first threshold;
cause the alarm device to silence the alarm in response to the detected second release event; and
in response to the detected second release event, provide the user additional time until the alarm is next sounded.

28. The system of claim 27, wherein the processor is further programmed to re-initialize the sit timer if the duration of the second release event is greater than a full release duration.

* * * * *